United States Patent [19]
Hoeschele et al.

[11] Patent Number: 5,380,897
[45] Date of Patent: Jan. 10, 1995

[54] TRI(PLATINUM) COMPLEXES

[76] Inventors: James D. Hoeschele, 6865 Montfort Dr., Canton, Mich. 48187; Yun Qu, 32 Pitkin St., Burlington, Vt. 05401; Nicholas Farrell, 20 Marsett Rd., Shelburne, Vt. 05482

[21] Appl. No.: 66,581

[22] Filed: May 25, 1993

[51] Int. Cl.⁶ .................. C07F 15/00; A61K 31/28; A61K 31/66
[52] U.S. Cl. .................. 556/137; 544/106; 544/358; 546/2; 546/152; 548/146; 548/335.1; 548/579
[58] Field of Search ........... 556/137; 514/492, 188; 546/2, 152; 544/358, 106; 548/146, 579, 335.1

[56] References Cited

U.S. PATENT DOCUMENTS

| | | | |
|---|---|---|---|
| 4,225,529 | 9/1980 | Hydes et al. | 260/429 R |
| 4,250,189 | 2/1981 | Hydes et al. | 424/287 |
| 4,565,884 | 1/1986 | Andrulis, Jr. et al. | 556/137 |
| 4,571,335 | 2/1986 | Taylor et al. | 424/131 |
| 4,797,393 | 1/1989 | Farrell et al. | 514/188 |
| 5,107,007 | 4/1992 | Farrell | 556/137 |

Primary Examiner—José G. Dees
Assistant Examiner—Porfirio Nazario-Gonzalez
Attorney, Agent, or Firm—Burns, Doane, Swecker & Mathis

[57] ABSTRACT

Novel tri(platinum) complexes containing three platinum coordination spheres coupled via diamine or triamine bridging agents are taught as well as methods for their preparation. These complexes are to be used as pharmaceutical agents, e.g., for the treatment of cancer and parasitic diseases.

48 Claims, No Drawings

TRI(PLATINUM) COMPLEXES

SUMMARY OF THE INVENTION

The invention relates to novel tri(platinum) complexes, methods for their preparation, and methods for their use as pharmacological agents, in particular, for treatment of cancer.

BACKGROUND OF THE INVENTION

The clinical use of platinum complexes such as cisplatin and carboplatin in cancer chemotherapy is well established in the art. A number of platinum complexes, such as PLATINOL ®, a registered trademark of cisplatin manufactured by Bristol Myers, Co., are used to treat testicular, ovarian, head and neck, and small-cell lung carcinomas. However, treatment with cisplatin may result in severe nephrotoxicity. A further clinical disadvantage is the problem of acquired drug resistance resulting in the tumor becoming refractory to treatment by the agent.

To overcome the nephrotoxic effects of cisplatin, a second-generation analog, carboplatin, was developed. PARAPLATIN ® is a registered trademark for carboplatin manufactured by Bristol-Myers, Co. Carboplatin, or [Pt(NH$_3$)$_2$ (CBDCA)] (where CBDCA is 1,1'cyclobutane dicarboxylate), is effective against the same spectrum of carcinomas as cisplatin, but exhibits a marked reduction in the nephrotoxic effects.

A number of different platinum compounds have been developed in an attempt to treat different tumors or carcinomas. For instance, U.S. Pat. No. 4,225,529 discloses the use of a cis coordination compound of platinum having four ligands which are selected from the group consisting of halides, sulphates, phosphates, nitrates, carboxylates, and same or different straight-chain amines which are coordinated to the platinum atom through their nitrogen atoms. These complexes are utilized for treating L-1210 leukemia in mice.

Also, U.S. Pat. Nos. 4,250,189, 4,553,502, and 4,565,884 relate to various Pt(II) and Pt(IV) complexes having anti tumor activity. These bis(platinum) complexes are linked with a carboxylate linkage such that upon administration of these complexes to the patient, the complexes undergo rapid hydrolysis to produce two cis monoplatinum moieties which are then delivered to the active site.

Additionally, U.S. Pat. No. 4,797,393, discloses a bis(platinum) complex which complex is delivered intact to the active site. This bis(platinum) complex has a bridging diamine or polyamine ligand and has primary or secondary amines or pyridine type nitrogens attached to the platinum complex, as well as two different or identical ligands which may be a halide, sulphate, phosphate, nitrate, carboxylate, substituted carboxylate or dicarboxylate. Also, commonly assigned application Ser. No. 07/713,105 relates to bis(platinum) complexes wherein the platinum moieties are linked by a diamine bridging agent, and wherein the platinum moieties are attached to ionic and neutral groups such that the net charge on the two platinum coordination spheres is 2+ or 1+.

However, critical problems still exist which limit the effective use of platinum complexes as therapeutics, most especially their narrow spectrum of activity against different tumors and the development of tumor cells which are resistant to the cytotoxic effects of cisplatin. (Loehrer et al., *Ann, Intern. Meal.*, (1984), 100, 704–711). For a general review relating to available platinum analogs, see, Christian, Michael, *Seminars in Oncology*, 1992, 19, 720–733.

It is generally believed that platinum complexes such as cisplatin manifest their biological activity through covalent interaction with DNA. In particular, cisplatin induces the formation of a range of adducts on DNA including monodentate adducts, bidentate adducts, such as GG or AG, and GNG intrastrand crosslinks. (Reedijk et al., *Structure and Bonding*, (1987), 67, 53–89). To a lesser extent, cisplatin also results in interstrand GG crosslinks and DNA-protein crosslinks. (Rahmouni et at., *Biochemistry*, (1987), 26, 7229–7234). These DNA lesions result in conformational changes which are reflected in bending and local unwinding of the DNA. These DNA lesions have been reported to inhibit the activity of various DNA polymerase. (Vallan et al., *Nucl. Acids Res.*, (1988), 16, 4407–4418; Pinto et al., *Proc. Natl. Acad. Sci*, (1985), 82, 4616–4619; and Gralla et at., *Cancer Res.*, (1987), 47, 5092–5096). The interstrand crosslink between two neighboring guanine bases has also been shown to inhibit RNA polymerase function. (Lemaire et al., *Proc. Natl. Acad. Sci.*, (1991), 88, 1982–1985). Accordingly, the cytotoxic effects of cisplatin are most likely attributable to the combined effects of these separate DNA lesions, rather than the result of any one specific lesion event.

Mono(platinum) and bis(platinum) complexes respectively containing one or two platinum atoms are known in the art. (See, e.g., U.S. Pat. Nos. 4,225,529, 4,250,189, 4,533,502, 4,565,884, 4,571,335 and 4,797,393). For example, mono(platinum) complexes include monomeric chloramine square-planar Pt(II) compounds which are four coordinate. The relative number of chloride and ammonia groups in such compounds may vary and these compounds may therefore be described by the general formula:

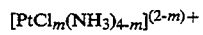

Thus, the structure of these compounds may vary from [Pt(NH$_3$)$_4$]$^{2+}$ where m=0 to PtCl$_4^{2-}$ where m=4. Since Cl is more substitution labile in comparison to ammonia, the complexes [PtCl$_2$(NH$_3$)$_2$] and [PtCl(NH$_3$)$_3$]Cl are considered bifunctional and monofunctional respectively, wherein the bi and mono prefixes refers to the number of leaving ligands. The charge of the complex is obtained by considering that the Pt(II) cation has a formal charge of +2 and thus requires a negative charge of −2 for charge neutralization. For example, when m=0, neutralization is provided by the presence of two chloride anions.

Coordinate bond formation results in electron pairing in the Pt—Cl bond. However, since the ammonia ligand is considered to be neutral, the bonding may be described as electron-pair donation from NH$_3$ to the empty orbitals on the Pt(II) atom. Thus, no electron sharing between the Pt and NH$_3$ group takes place. Because of this absence of electron sharing, the number of neutral ligands does not affect the overall charge in the Pt coordination sphere. Thus, [Pt(NH$_3$)$_4$]$^{2+}$ is formally a 2+ cation requiring non-coordinating anion or anions, or counter-anions, having a net negative charge of 2− for neutralization of the complex. For example, neutralization can be provided by two mononegatively charged anions (e.g., NO$_3^-$, Cl$^-$, PF$_6^-$, BF$_4^-$, and monocarboxylates having the general formula RCOO$^-$) or a single dinegatively charged anion (e.g., $SO_4^{2-}$, dicarboxylates having the general formula $(RCOO)_2^{2-}$). Therefore, by the same principles, $[PtCl_2(NH_3)_2]$ is a neutral complex. Moreover, in some cases, Pt(II) anions may serve as counter-anions. An example is the well known Magnus salt $[Pt(NH_3)_4]^{2+}$ $[PtCl_4]^{2-}$.

It is noted that artionic ligands such as Cl− may be either coordinately bound (i.e., forming a Pt—Cl bond) or may act as a counter-anion without any need for covalent bond formation. The exact form that anions such as Cl− are comprised in a given platinum complex depends both on theoretical considerations (kinetic vs. thermodynamic effects) and the actual synthetic procedures utilized to make the complex (e.g., the extent of reaction, acidity, concentration of the particular anion, such as the concentration Cl− which is contained in the reaction mixture). These considerations are applicable to other anionic and neutral ligands as well.

Examples of neutral ligands typically comprised in monoplatinum complexes include, e.g., olefins such as ethylene ($C_2H_4$), propene and 2-butene; phosphines ($PR_3$), sulfides ($SR_2$), sulfoxides ($R_2SO$), ammonia ($NH_3$), primary amines ($RNH_2$) and heterocyclic amines such as pyridine or quinoline. Examples of typical anionic ligands contained in platinum complexes include halides (e.g., Cl−, Br−, I−) and pseudohalides such as SCN−, CN−, and $NO_3^-$. The term "pseudohalide" comprises the definition found on page 560 of "Advanced Inorganic Chemistry" by Cotton and Wilkinson). Alternative suitable pseudohalides may be found in many standard inorganic chemistry books. e.g., such as *Inorganic Chemistry* by Cotton and Wilkinson.

The fact that the overall charge of monoplatinum complexes depends on the relative number of neutral and anionic ligands which are bound to the Pt(II) metal, e.g., $NH_3$ and Cl− ligands, is equally applicable for polynuclear complexes (which contain more than one Pt(II) coordinate spheres), and for Pt(IV) containing complexes wherein the oxidation state of the platinum moiety is 4+. For example, dinuclear complexes where two equivalent Pt(II) coordination spheres are linked by a diamine bridging agent may be represented by the general formula $[\{PtCl_m(NH_3)_{3-m}\}_2 \text{(diamine)}]^{2(2-m)+}$. Thus, when m=2, and two bifunctional coordination spheres are present, the compound is neutral. In contrast, when m=1, only monofunctional coordination spheres are present and the Pt moiety has a formal charge of 2+ which must be counterbalanced by one or more counter-anions having a net charge of 2−.

OBJECTS OF THE INVENTION

As discussed supra, mono(platinum) and bis(platinum) complexes and the use thereof as cancer therapeutic agents is known in the art.

In contrast, the present invention describes the synthesis of tri(platinum) complexes containing three platinum coordination spheres wherein the platinum atoms are linked by diamine or triamine bridging agents. The nature of the bridging agent may be chosen to produce linear or "bent" tri(platinum) units. Because of the presence of three platinum atoms, administration of these complexes should allow for the delivery of three cisplatin units or platinum-amine units to the same region of DNA, a feature unavailable to conventional mono(platinum) or bis(platinum) complexes. Accordingly, tri(platinum) complexes should provide for enhancement of DNA adduct formation in comparison to mono(platinum) and bis(platinum) complexes and consequently should result in enhanced cytotoxic effects since minimal bifunctional DNA adduct formation is believed to be the mechanism by which platinum complexes mediate cytotoxicity.

In its broadest aspect, it is an object of this invention to provide tri(platinum) complexes wherein three platinum coordination spheres are linked by diamine or triamine bridging agents, and wherein the oxidation states of such platinum moieties are 2+ or 4+ or a combination thereof.

It is a further object of the invention to provide pharmaceutical compositions containing tri(platinum) complexes wherein the platinum coordination spheres are linked by diamine or triamine bridging agents.

It is another object of the invention to provide methods for synthesizing tri(platinum) complexes wherein the platinum coordination spheres are linked by diamine or triamine bridging agents.

It is a specific object of the invention to provide tri(platinum) Pt(II) complexes of the general formula:

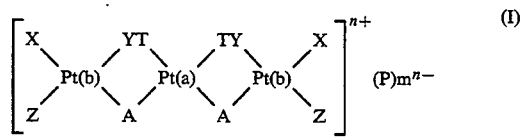

and

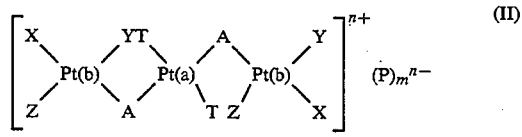

and

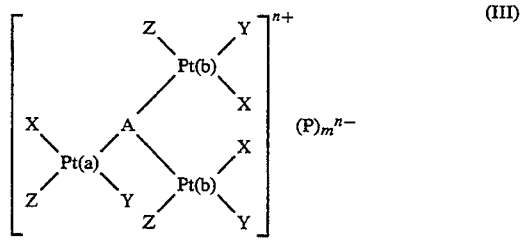

where X, Y, Z and T are neutral and/or anionic ligands, which may be the same or different, with the proviso that at least one of X, Y or Z on each Pt(b) must be an anionic ligand; A comprises a diamine or triamine bridging agent, n represents the net charge of the three platinum coordination spheres, P represents one or more counter-anions which may or may not be required depending upon whether or not the three platinum coordination spheres have a net charge, and n− represents the net charge of the counter-anions (if present) wherein the number and charge of such counter-anions is selected such that the overall tri(platinum) complex is neutral.

It is another specific object of the invention to provide tri(platinum) complexes wherein the platinum moieties comprised therein exist in the Pt(IV) oxidation state, or as a combination of Pt(II) and Pt(IV) oxidation states. Specifically, such tri(platinum) complexes will comprise the formula:

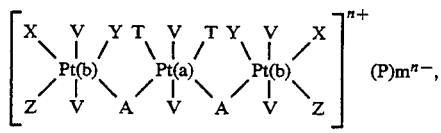

(IV)

and

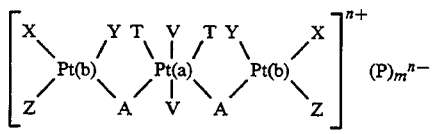

(V)

and

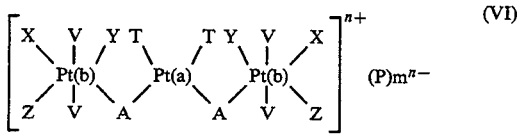

(VI)

wherein X, Y, Z, A and T are defined as set forth supra, and wherein the V moieties are anionic groups, preferably (OH)—, (Cl)— or $O_2CR$.

Pt(IV) complexes are known in the art. For example, tetraplatin (ormaplatin), cis-[(PtC$_4$(dach)] and CHIP cis, cis, trans-[PtCl$_2$(i-PtNH$_2$)$_2$(OH)$_2$] are examples of Pt(IV) complexes which are known. Oxidation of platinum to its Pt(IV) form is typically achieved by treatment with $H_2O_2$ and/or $Cl_2$. For example, treatment of cis-[PtCl$_2$(NH$_3$)$_2$] with either $H_2O_2$ and/or $Cl_2$ as an oxidizing agent gives cis, cis, trans-[PtCl$_2$(NH$_3$)V$_2$], wherein V=OH, Cl. Those skilled in the art will understand that when V=OH, further substitution of the OH group with carboxylate to obtain V=$O_2CR$ may be achieved, wherein R may be a linear or branched alkyl or alkenyl group preferably $C_1$-$C_{18}$, an aromatic group, or an aralkyl group. It is generally recognized in the art that when V=$O_2CR$ that such platinum anticancer complexes exhibit applicability for oral administration.

As with the tri(platinum) complexes of formula (I), (II) and (III), in the Pt(IV) tri(platinum) complexes P is a counter-anion or counter-anions which may be the same or different, m represents the number of such counterions, and n— represents the overall change of such counteranions and is such that the resultant tri(platinum) complex is neutral. In the case where the three platinum moieties have a net neutral charge, no counteranions will be present.

It is another specific object of the invention to provide pharmaceutical compositions containing at least one of the tri(platinum) complexes of formula (I), (II), (III), (IV), (V) or (VI).

It is a further object of the invention to provide a method of use of tri(platinum) complexes of formula (I), (II), (III), (IV), (V) or (VI) for therapeutic use, e.g., for treatment of tumors or parasitic conditions.

It is still another specific object of the invention to provide a method for synthesizing tri(platinum) complexes of the general formula (I), (II) or (III). (VI) where the formed change of the platinum cations comprised therein is 4+, or a combination of 4+ and 2+ oxidation states.

The subject tri(platinum) complexes, by virtue of their containing three platinum coordination spheres, should provide for enhanced cytotoxic activity relative to currently available mono- and bis(platinum) complexes.

DETAILED DESCRIPTION OF THE INVENTION

The present invention provides a novel class of tri(platinum) complexes which should exhibit enhanced cytotoxic activity than currently available platinum complexes. In particular, such tri(platinum) complexes will comprise the general formula:

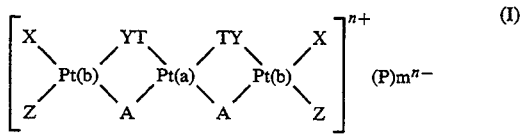

(I)

and

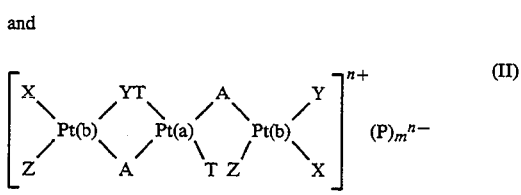

(II)

and

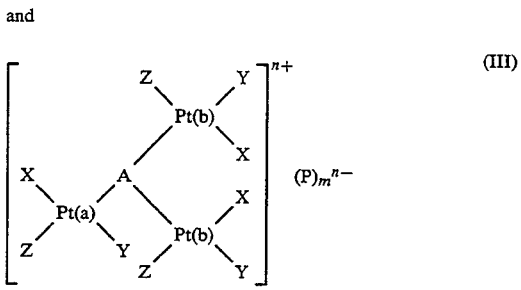

(III)

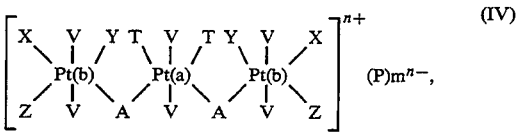

(IV)

and

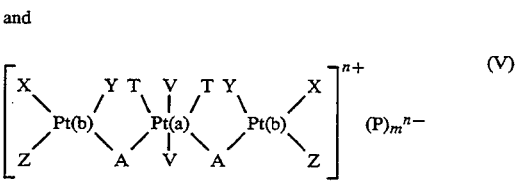

(V)

and

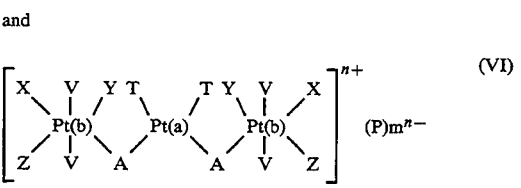

(VI)

where X, Y, Z and T are neutral and/or anionic ligands, with the proviso that at least one of X, Y or Z on each Pt(b) must be an anionic ligand; A comprises a aliamine or triamine bridging agent, n comprises the net charge on the three platinum coordination spheres, P, if required, comprises one or more counter-anions, which may be the same or different; m comprises the number of such counter-anions, and n— comprises the net negative charge of the counter-anions which are selected such that the overall charge of the tri(platinum) complex is zero. In the tri(platinum) complexes of formulae (IV), (V) or (VI), V comprises a monovalent anionic group, e.g., a halide, pseudohalide, carboxylate, hydroxide. Preferably, the anionic groups will be (OH)—, (Cl−) or O₂CR.

Preferably, X, Y, Z and T will be selected from neutral ligands selected from the group consisting of NH₃, primary amines, secondary amines, heterocyclic amines, sulfoxides (R'R"SO), and the anionic ligands will preferably be selected from the group consisting of halides, pseudohalides (where "pseudohalide" comprises the definition found on page 560 of "Advanced Inorganic Chemistry" by Cotton and Wilkinson), carboxylates, monovalent anions such as $PF_6^-$, $BF_4^-$, anionic ligands and divalent anions such as $SO_4^{-2}$. As noted, at least one of X, Y or Z on each Pt(b) will comprise an anionic ligand, preferably a chloride group.

The primary amines comprised in the subject tri(platinum) complexes will preferably comprise alkyl amines of the formula $NH_2—R_1$ where $R_1$ comprises a linear or branched $C_1–C_8$ alkyl group, or a $C_3–C_6$ cycloalkyl group such as cyclopropyl, cyclobutyl, cyclopentyl, cyclohexyl or will comprise a —CH₂OH group.

The secondary amines suitable as neutral ligands in the subject tri(platinum) complexes will preferably comprise alkyl amines having the general formula $NH(R_1)_2$ where $R_1$ again preferably comprises a $C_1–C_8$ linear or branched alkyl group, a $C_3–C_6$ cycloalkyl group such as cyclopropyl, cyclobutyl, cyclopentyl, cyclohexyl or a CH₂OH group.

The sulfoxides, R'R" SO, which are useful as neutral ligands in the subject tri(platinum) compound include any combination of R' and R" groups, wherein R' and R" comprise alkyl or aromatic groups, preferably Me, Ph, X—Ph (wherein X may, e.g., be a halide, methoxy, or hydroxyl group), CH₂Ph, Et, n-propyl, iso-propyl, or n-butyl.

Suitable heterocyclic amines suitable as neutral ligands in the subject tri(platinum) compounds include, e.g., compounds having saturated or unsaturated heterocyclic tings, such as pyridine, quinoline, isoquinoline, imidazole, thiazole, substituted pyridine, substituted quinoline, substituted isoquinoline, substituted thiazole, piperidine, pyrrolidine, morpholine, and N-alkyl or N-acyl-piperazine.

The anionic ligands suitable for use in the subject tri(platinum) complexes include, e.g., halides, pseudohalides, carboxylates, and mono- and divalent anions. Preferably, the anionic ligands will comprise halides, and most preferably, chlorides. However, other halides such as bromide and iodide may also be utilized as the anionic ligands.

Pseudohalides suitable for use in the inventive tri(platinum) complexes will include, e.g., $SCN^-$, $CN^-$, $NO_3^-$, or any of those disclosed in standard organic textbooks such as "Advanced Inorganic Chemistry" by Cotton and Wilkinson. Typical examples of carboxylate groups which may be utilized in the subject tri(platinum) complexes includes, e.g., acetate, propionate, butyrate, chloroacetate, hydroxyacetate, benzoate and chelating dicarboxylate groups such as oxalate, malonate, substituted malonate, succinate, glutarate, and phthalate.

Preferably, such substituted malonate groups will have the general formula:

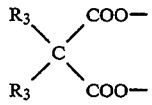

wherein $R_3$ are the same or different and include, e.g., hydrogen (with the proviso that both $R_3$ cannot be hydrogen), $C_1–C_8$ linear or branched alkyl groups such as methyl, ethyl, n-propyl, iso-propyl, n-butyl, sec-butyl, tert-butyl, n-pentyl, n-hexyl, n-heptyl, n-octyl or both $(R_3)_2$ groups taken together represent a $C_3–C_6$ cycloalkyl such as cyclopropyl, cyclobutyl, cyclopentyl, cyclohexyl or a —CH₂OH group.

As noted, A in the above formulae comprises a diamine or triamine bridging agent. Such aliamine bridging agents will comprise the general formula $H_2N—R—NH_2$, where R will preferably comprise a linear or branched alkyl or alkenyl group, preferably $C_1–C_{18}$, including e.g., methyl, ethyl, n-propyl, iso-propyl, n-butyl, sec-butyl, tert-butyl, n-pentyl, n-hexyl, n-octyl, oleyl, linoleyl; a cycloalkyl group, preferably a $C_3–C_6$ cycloalkyl such as cyclopropyl, cyclobutyl, cyclopentyl, or cyclohexyl; a substituted phenyl such as ortho, meta or para tolyl, mono- or di-halogen substituted phenyl groups, preferably chloride, bromide, or fluoride; mono- and dimethoxy substituted phenyl groups; aralkyl groups, preferably $C_7$ to $C_{10}$ aralkyl groups such as phenylmethyl, phenylethyl and phenylpropyl; and perfluoroalkyl groups such as trifluoromethyl and trifluoroethyl.

More preferably, the bridging diamine A will comprise the general formula:

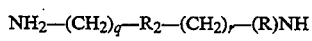

$NH_2—(CH_2)_q—R_2—(CH_2)_r—(R)NH$ wherein R includes the groups named above, and q and r are integers which may be the same or different and range from between 1 and 4 inclusive, and wherein $R_2$ is preferably selected from among the following groups: —CH₂—, —CHOH—, —CO—, —CHOR—, —OC(O)(O), —SO₂—, —OS(O₂)O—, and —OP(O)(OH)O—.

Most preferably, the diamine bridging agent will comprise the general formula $—NH_2—(CH_2)_s—NH_2$, wherein S is an integer which ranges from 2 to 9 inclusive.

The triamine bridging agent will preferably comprise the general formula

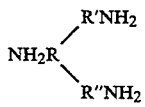

wherein R, R' and R" may be the same or different and may include linear or branched alkyl or alkenyl groups, cycloalkyl, aralkyl, perfluoroalkyl and aromatic groups. R, R' and R" will preferably comprise $C_1–C_{18}$ linear or branched alkyl or alkenyl groups, e.g., methyl, ethyl, n-propyl, iso-propyl, n-butyl, sec-butyl, tert-butyl, n-pentyl, n-hexyl, n-octyl, oleyl, linoleyl; cycloalkyl groups, preferably $C_3–C_6$ cycloalkyl groups such as cyclopropyl, cyclobutyl, cyclopentyl, or cyclohexyl; substituted phenyls such as ortho, meta or para tolyl, mono- or di-halogen substituted phenyl groups, and dimethoxy substituted phenyl groups; aralkyl groups, preferably $C_7$ to $C_{10}$ aralkyl groups such as phenylmethyl, phenylethyl and phenylpropyl; and perfluoroalkyl groups such as trifluoromethyl and trifluoroethyl. In the most preferred embodiment, the triamine bridging agent will comprise:

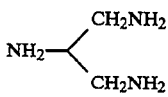

The selection of triamine bridging agents having such a "bent" structure provides for tri(platinum) complexes having the general structure set forth in formula (III).

As noted previously, P comprises one or more counter-anions which may or may not be present depending upon whether the three platinum coordination spheres have a net charge. The "m" refers to the number of such counter-anions, and will typically range from 0 to 4 inclusive. The number of charge of such counter-anions will be such that the overall charge of the tri(platinum) complex is zero. Examples of suitable counter-anions include, e.g., halides, including $Br^-$, $Cl^-$, and $I^-$, and other anionic ligands such as $NO_3^-$, $SO_4^{2-}$, $ClO_4^-$, carboxylates such as the mono- and dicarboxylates enumerated above, and $PF_6^-$, and $SbF_6^-$. Such a list is meant to be exemplary and by no means exhaustive.

The subject tri(platinum) complexes will preferably be synthesized by a three step procedure.

In order to link two platinum coordination spheres in a stereospecific fashion, it is first necessary to prepare a precursor monomer containing a "dangling" and diamine bridging agent, $H_2N-R-NH_2$ which contains one uncomplexed end which comprises either a blocking agent (e.g., Boc, tertrabutoxy carbonyl) or a $NH_3^+$ salt. Subsequent reaction with a suitable target gives the dinuclear species:

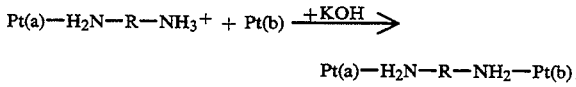

In contrast, when preparing the subject tri(platinum) complexes containing three cis-Pt(amine)$_2$ units, the general preparation of such complexes will involve synthesis of a suitable precursor containing two mono-protected diamines (step 1), followed by treatment with an acid, such as dilute HCl, to give the corresponding protonated amine $RNH_3^+Cl^-$, which may then be used as a source for further metallation (step 2); followed by reaction with two equivalents of an appropriate Pt(b) target molecule to afford the desired product (step 3):

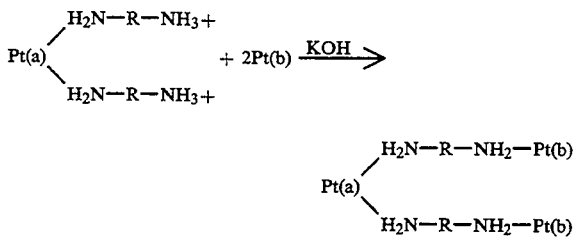

The initial Pt(a) precursor synthesized which contains two mono-protected diamines will vary dependent upon the desired "T" moieties, and the desired orientation thereof in the final tri(platinum) complex, and wherein T comprises one of the anionic or neutral ligands discussed supra. Examples of suitable Pt(a) precursors include, e.g., cis or trans-[PtCl$_2$(H$_2$N—R—NH$_3$Cl)$_2$], cis or trans-[Pt(NH$_3$)$_2$(H$_2$N—R—NH$_3$Cl)$_2$]$^{2+}$, cis or trans-[PtCl$_2$(H$_2$N—CH(CH$_2$NH$_3$)$_2$Cl$_2$], cis or trans-[PtCl(NH$_3$)(H$_2$N—R—NH$_3$Cl)$_2$]$^+$ and cis-[Pt(mal)(H$_2$N—R—NH$_3$Cl)$_2$] (where real is malonate or any dicarboxylate).

In producing the tri(platinum) complexes of formula (III) the Pt(a) precursor will preferably have a "bent" structure by virtue of the triamine bridging agent which is attached thereto. In particular, the Pt(a) precursor will preferably comprise the general structure:

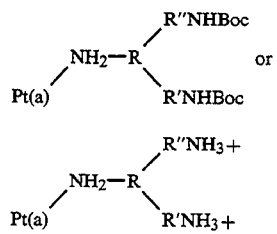

For example, a suitable Pt(a) precursor ligand comprises:

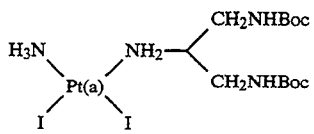

This Pt(a) precursor will then be reacted with two equivalents of an appropriate Pt(b) target molecule to produce the desired tri(platinum) complex. Similarly, the Pt(b) target molecule of step 3 which is to be reacted with the protonated amine obtained in step 2, will be selected based upon the desired X, Z and Y moieties and the orientation thereof in the final tri(platinum) complex. Examples of suitable Pt(b) target molecules include, e.g., [PtLCl$_3$]$^-$ (wherein L is NH$_3$, RNH$_2$, R'R''SO, py), cis- or trans-PtCl$_2$(NH$_3$)$_2$], and cis- or trans-[PtCl$_2$(RNH$_2$)$_2$].

For example, in order to synthesize cis-[{cis-PtCl$_2$(NH$_3$) ($\mu$-H$_2$N(CH$_2$)$_4$NH$_2$)}$_2$PtCl$_2$] the following steps are effected:

Step 1: Preparation of Platinum (Pt(a) Precursor containing two Mono-protected Diamines

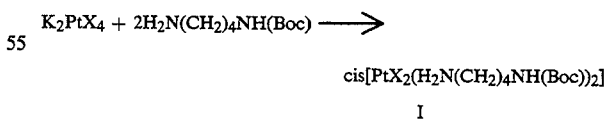

I

X in this formula represents an anion, preferably a halide. For example, when X=Cl, the precursor is the commercially available K$_2$PtCl$_4$. Where X=Br or I, the complex is prepared in situ by addition of four equivalents of X$^-$ (in the form of a simple salt NaX or KX) by the method of Dhara (Dhara, *Indian J. Chem.* (1970), 8, 193).

Step 2: Treatment of Platinum Pt(a) Diamine Precursor (I) With Acid to Obtain Protonated Diamine (II)

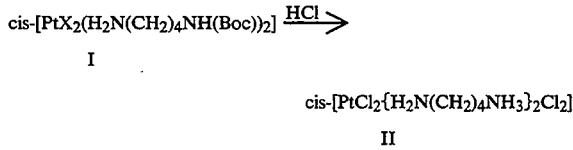

I cis-[PtCl₂{H₂N(CH₂)₄NH₃}₂Cl₂]

II

Step 3: Preparation of Tri(platinum) Complex by Reacting Protonated Diamine (II) with Target Pt(b) Compound

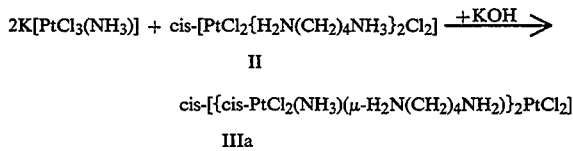

cis-[{cis-PtCl₂(NH₃)(μ-H₂N(CH₂)₄NH₂)}₂PtCl₂]

IIIa

For example, herein the target molecule selected comprises K[PtCl₃(NH₃)] because substitution occurs cis relative to the NH₃ ligand. However, the precursor and target molecule will of course vary dependent upon the desired structure of the tri(platinum) complex, in particular, the desired selections for X, Y, Z and T and their respective position on the resultant tri(platinum) complex.

The tri(platinum) complexes of formula (IV), (V) and (VI) will be prepared substantially as described except that the precursor Pt(a) monomers or Pt(b) target molecules used to produce the tri(platinum) complex will comprise a Pt(IV) oxidation state or the tri(platinum) complex of formula (I) or (II) above will be oxidized to produce the corresponding Pt(IV) containing tri(platinum) complexes. In the case of the tri(platinum) complexes of formula (IV) wherein all three platinum moieties comprise a 4+ oxidation state, the Pt(II) tri(platinum) complex of formula (I), (II) or (III) may be oxidized to obtain a complex having three Pt(IV) units.

For the tri(platinum) complexes of formula (V) which comprise a single Pt(IV) units, the Pt(a) precursor having a 2+ oxidation state will be oxidized to produce the corresponding Pt(a) precursor having a 4+ oxidation state. This will be then linked with two Pt(b) target molecules as described.

For the tri(platinum) complexes of formula (VI) which comprise two Pt(IV) units, the Pt(b) target molecule will be oxidized to the 4+ oxidation state prior to linking with a Pt(a) precursor having the 2+ oxidation state.

The tri(platinum) complexes of the present invention are intended for pharmaceutical application. Given the presence of three platinum coordination spheres, they should exhibit greater cytotoxic activity than currently available platinum complexes. The subject complexes will be used for treatment of the identical diseases and conditions which cisplatin is used to treat. This includes the treatment of tumors, radiation sensitization or potentiation (Douple et al, *Cisplatin Current Status and Developments*, Eds. A. W. Prestayk et al, Academic Press, 125 (1980); Douple et al, *Platinum Metals Res.*, 1985, 29, 118) and treatment of parasitic diseases such as sleeping sickness (Farrell et al, *Biochem, Pharmacol.*, 1984, 33, 961). The complexes of the present invention will preferably be administered at the same dosage levels of cisplatin, while taking into account the LD₅₀, value of the particular tri(platinum) complex. Generally, the tri(platinum) complex will be combined with a pharmaceutically acceptable carrier. For example, the complex and carrier may be formulated for parenteral or oral administration by methods well known in the art. For instance, see Remington's Pharmaceutical Sciences for suitable pharmaceutically acceptable carriers and formulation methods.

Given their structures the subject tri(platinum) complexes should comprise utility in the treatment of cancer, parasitic disorders and other conditions wherein platinum complexes find current therapeutic usage. The therapeutic efficacy of a particular tri(platinum) complex will be evaluated by standard methods. For example, the cytotoxic activity of a particular tri(platinum) complex may be evaluated in vitro based on its cytotoxicity agains L1210 cancer cells, P388 cancer cells, or L1210 or P388 cancer cells resistant to cisplatin. The L1210 assay in particular, is an accepted method for screening platinum complexes for therapeutic activity.

Those tri(platinum) complexes which exhibit cytotoxic activity, e.g., against L1210 cells, will then be tested in vivo in animals, e.g., nude mice containing implanted human tumors. Those tri(platinum) complexes which exhibit in vivo activity without substantial adverse effects (e.g., nephrotoxicity) will be tested clinically.

In order to fully illustrate the present invention and the advantages thereof, the following specific examples are given, it being understood that these examples are intended only to be illustrative without serving as a limitation on the scope of the present invention.

EXAMPLE 1

Preparation of cis-[{cis-PtCl₂(NH₃)(μ-H₂N(CH₂)₄NH₂)}₂PtCl₂]

The preparation of this compound is shown schematically supra. The actual experimental procedures used by the present inventor to synthesize this complex are described as follows:

COMPLEX I. cis-[PtCl₂(H₂N(CH₂)₄NH(Boc))₂].

To a filtered solution of 0.8579g K₂PtCl₄ dissolved in 7 mL water, 0.8371 g H₂N(CH₂)₄NH(Boc)) in 5 mL water was added / dropwise. The mixture was stirred for 5 h, during which time a cream colored solid precipitated. The solid was collected on a sintered glass funnel, washed with water and acetone and dried. δ(¹⁹⁵Pt) in DMF = −2226 ppm. Anal. Calcd for C₁₆H₄₀N₄Cl₂O₄Pt: C,33.65; H,6.27; N,8.72; Cl,10.83. Found: C,33.90; H,6.43; N,8.80; Cl,11.23.

COMPLEX II. cis-[PtCl₂(H₂N(CH₂)₄NH₃)₂Cl₂.

0.4516 g cis-[PtCl₂(H₂N—R—NH(Boc))₂] was suspended in 10 mL MeOH with 2mL water. Ten millimeters of concentrated HCl was added slowly to the stirred suspension. After some time the cream colored solid dissolved to give a yellow solution. The solution was taken to dryness in a stream of nitrogen, and the resulting yellow solid washed with acetone and dried in a drying pistol over boiling acetone. Complex II is quite soluble in water.

Characterization for II: Anal. Calcd for C₈H₂₆N₄Cl₄Pt: C,18.65; H,5.09; N,10.87; Cl,27.52. Found: C,18.89; H,5.40; N,10.76; Cl,27.70. NMR in D₂O: δ(¹H): 3.04, 2.77, 1.79 ppm; δ(¹⁹⁵Pt): −2239 ppm. COMPLEX IIIa. cis-[{cis-PtCl₂(NH₃)(μ-H₂N(CH₂)₄NH₂)}₂PtCl₂]

0.713 g cis-[PtCl₂(H₂N—R—NH₃)₂Cl₂] was dissolved in 3 mL H₂O and a solution of 1.5828 g K[PtCl₃(NH₃)] in 12 mL H₂O was added. 0.18 g KOH in 5 mL H$_2$O was added dropwise with stirring. A yellow precipitate began to form within 3 minutes. After an hour the solid IIIa was filtered off, washed with water and acetone and dried.

Anal. Calcd for C$_8$H$_{30}$N$_6$Cl$_6$Pt$_3$ (IIIa): C,9.53; H,3.00; N,8.33; Cl,21.10. Found: C,9.34; H,2.90; N,8.02; Cl,20.30.

COMPLEX IIIc. cis-[{cis-Pt(mal)(NH$_3$)($\mu$-H$_2$N(CH$_2$)$_4$NH$_2$)}$_2$Pt(mal)]

The malonate was prepared by the standard method of Kraker et al. (*J. Med. Chem.* (1992), 35, 4526) by stirring a suspension of IIIa in H$_2$O with three equivalents of silver malonate for 48 h. The AgCl was precipitated and filtered, the flitrate evaporated to half volume and the product precipitated with acetone. The white complex was then recrystallized from H$_2$O/acetone.

Anal. Calcd for C$_{17}$H$_{36}$N$_6$O$_{12}$Pt$_3$.3H$_2$O (IIIc): C,17.67; H,3.66; N,7.27. Found: C, 17.66; H, 3.72; N, 6.57. MS(FAB) + parent ion: 1102 (Calcd 1102).

EXAMPLE 2

Preparation of cis-[{cis-PtCl$_2$(NH$_3$)($\mu$-H$_2$N(CH$_2$)$_4$NH$_2$)}$_2$PtNH$_3$)$_2$]Cl$_2$ As discussed supra, the synthetic scheme detailed above for preparing the subject tri(platinum) complexes is applicable to a wide range of Pt(a) precursors and Pt(b) target molecules, dependent upon the desired X, Y, Z and T moieties and their desired orientation in the resultant tri(platinum) complexes. For example, reaction of cis-[PtCl$_2$(NH$_3$)$_2$] with H$_2$N(CH$_2$)$_4$(Boc) affords the tetra-amine:

Step 1

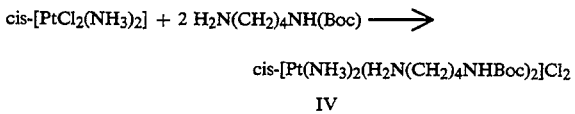

and
Step 2

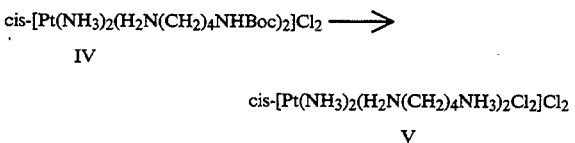

Reaction of V with K[PtCl$_3$(NH$_3$)] gives the cation VIa containing two cis-[PtCl$_2$(amine)$_2$] groups linked through a [Pt(amine)$_4$] unit:

Step 3

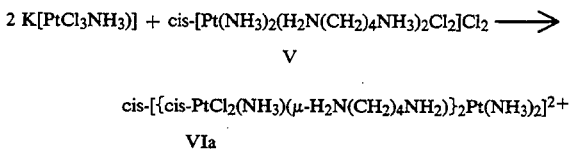

The trimeric complex VIa initially precipitates with the [PtCl$_3$(NH$_3$)] counter-anion as evidenced by elemental analysis and a $^{195}$Pt NMR peak at −1881 ppm. Metathesis of VIa to form VIb may be achieved by treatment of VIa with [Pt(NH$_3$)$_4$]Cl$_2$ in H$_2$O which selectively precipitates the highly insoluble [Pt(NH$_3$)$_4$][PtCl$_3$(NH$_3$)]$_2$ salt leaving the tri(platinum) cation in solution as the chloride salt.

Experiential procedures for Example II.

COMPLEX IV. cis-[Pt(NH$_3$)$_2$(H$_2$N(CH$_2$)$_4$NHBoc)$_2$]Cl$_2$ 0.45 grams of cis-DDP was suspended in 75 mL H$_2$O at 70°-80° C. with stirring. 0.6 grams of H$_2$N(CH$_2$)$_4$NHBoc (slight excess of 1:2 stoichiometry) was dissolved in 10 mL of H$_2$O and was added to the suspension. Stirring was continued for 4 h at 70°-80° C. during which time a colorless solution formed. Upon cooling, the solution was filtered with activated carbon through celite. The tiltrate was then evaporated to 2 mL and 50 mL acetone was added. After cooling at 3° C. overnight, the white product precipitated and was filtered off and washed with acetone.

Anal. Calcd for C$_{16}$H$_{46}$N$_6$Cl$_2$O$_4$Pt: C,31.95; H,6.85; N,12.42; Cl,10.48. Found: C,31.75; H,6.90; N,12.12; Cl,10.29. NMR in D$_2$O: $\delta$($^1$H): 3.08, 2.72, 1.74, 1.54, 1.43 ppm; $\delta$($^{195}$Pt): −2681 ppm.

COMPLEX V. cis-[Pt(NH$_3$)$_2$(H$_2$N(CH$_2$)$_4$NH$_3$)$_2$Cl$_2$]Cl$_2$ 0.8 grams of Complex IV was suspended in 10 mL MeOH and 2 mL H$_2$O. Concentrated HCL (10 mL) was added slowly to the stirred suspension. After two hours the solution was filtered and the flitrate evaporated to dryness. MeOH (200 mL) was added with stirring for 2 h. and the solution filtered. The tiltrate was evaporated to 10 mL and upon cooling the product precipitated.

Anal. Calcd for C$_8$H$_{32}$N$_6$Cl$_4$Pt: C,17.49; H,5.96; N,15.30; Cl,25.82. Found: C,17.20; H,5.96; N,15.01; Cl,25.53. NMR in D$_2$O: $\delta$($^1$H): 3.02, 2.75, 1.73 ppm; $\delta$($^{195}$Pt): −2651 ppm.

COMPLEX VIa. cis-[{cis-PtCl$_2$(NH$_3$)($\mu$-H$_2$N(CH$_2$)$_4$NH$_2$)}$_2$Pt(NH$_3$)$_2$][PtCl$_3$(NH$_3$)]$_2$ 0.1 grams of Complex V was dissolved in 2 mL H$_2$O and 0.5 mL 1M KOH was added. The solution was added dropwise to a solution of K[PtCl$_3$(NH$_3$)] (0.15 g) in 5 mL H$_2$O with stirring for 2 h. The solution was filtered and 30 mL MeOH added, precipitating a light yellow product.

Anal. Calcd. for C$_8$H$_{42}$N$_{10}$Cl$_{10}$Pt$_5$: C,5.97; H,2.63; N,8.71; Cl,22.04. Found: C, 6.72; H, 2.57; N, 8.71; Cl,20.89.

COMPLEX VIb. cis-[{cis-PtCl$_2$(NH$_3$)($\mu$-H$_2$N(CH$_{24}$NH$_2$)}$_2$Pt(NH$_3$)$_2$]Cl$_2$ 0.3 grams of Complex VIa was dissolved in 40 mL H$_2$O at 40°-50° C. and 0.1 g of [Pt(NH$_3$)$_4$]Cl$_2$ in 1 mL H$_2$O was added to it. Cooling the solution to 3° C. overnight gave a golden yellow precipitate [Pt(NH$_3$)$_4$][PtCl$_3$(NH$_3$)]$_2$ and the supernatant was decanted and evaporated to half volume. The supernatant was again decanted from a further precipitate of the tetraamine salt and evaporated to 5 mL. Addition of 20 mL MeOH and cooling overnight gave a small quantity of product.

Anal. Calcd for C$_8$H$_{36}$N$_8$Cl$_6$Pt$_3$ (VIb): C,9.22; H,3.48; N,10.75; Cl,20.41. Found: C, 8.99; H, 3.61; N, 10.28; Cl,20.25.

While the invention has been described in terms of various preferred embodiments, one skilled in the art will appreciate that various modifications, substitutions, omissions, and changes may be made without departing from the spirit thereof. Accordingly, it is intended that the scope of the present invention be limited solely by the scope of the following claims.

In the claims:

1. A tri(platinum)complex of the general formula:

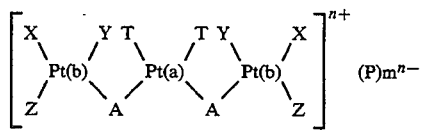 (I)

or

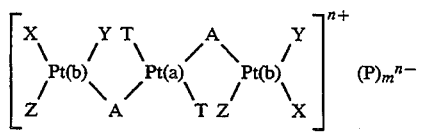 (II)

or

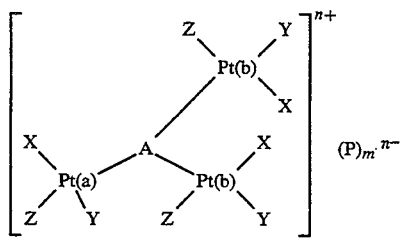 (III)

where X, Y, Z and T are neutral and/or anionic ligands, which may be the same or different, with the proviso that at least one of the X, Y or Z on each Pt(b) must be an anionic ligand, A is a diamine or triamine bridging agent, n represents the net charge of the three platinum coordination spheres, P represents one or more counterions which may or may not be present dependent upon whether the three platinum coordination spheres have a net charge, and n— represents the net charge of the counterions and is such that the resultant tri(platinum) complex is neutral.

2. The tri(platinum) complex of claim 1, wherein the neutral ligands are selected from the group consisting of $NH_3$, primary amines, secondary amines, heterocyclic amines and sulfoxides.

3. The tri(platinum) complex of claim 2, wherein the heterocyclic amines are selected from the group consisting of pyridine, quinoline, isoquinoline, imidazole, thiazole, piperidine, pyrrolidine, morpholine, and N-alkyl or N-acyl-piperazine.

4. The tri(platinum) complex of claim 1, wherein the primary amines have the general formula $NH_2$—$R_1$ and $R_1$ is selected from the group consisting of linear or branched $C_1$–$C_8$ alkyl groups, $C_3$–$C_6$ cycloalkyl groups, and —CHOH.

5. The tri(platinum) complex of claim 4, wherein the $C_3$–$C_6$ cycloalkyl groups are selected from the group consisting of cyclopropyl, cyclobutyl, cyclopentyl, and cyclohexyl.

6. The tri(platinum) complex of claim 2, wherein the secondary amines have the general formula $NH(R_1)_2$ and $R_1$ is selected from the group consisting of $C_1$–$C_8$ linear or branched alkyl groups, $C_3$–$C_6$ cycloalkyl groups, and a CHOH group.

7. The tri(platinum) complex of claim 2, wherein the sulfoxides have the general formula R'R"SO and R' and R" may be the same or different and are selected from the group consisting of methyl, phenyl, substituted phenyl, methylphenyl, ethyl, n-propyl, iso-propyl and n-butyl.

8. The tri(platinum) complex of claim 1, wherein the anionic ligands are selected from the group consisting of halides, pseudohalides, carboxylates, and mono- and divalent anions.

9. The tri(platinum) complex of claim 8, wherein the pseudohalides are selected from the group consisting of $SCN^-$, $CN^-$ and $NO_3^-$.

10. The tri(platinum) complex of claim 8, wherein the carboxylate groups are selected from the group consisting of acetate, propionate, butyrate, chloroacetate, hydroacetate, benzoate, and chelating dicarboxylate groups.

11. The tri(platinum) complex of claim 10, wherein the chelating dicarboxylate groups are selected from the group consisting of oxalate, malonate, substituted malonate, succinate, glutarate and phthalate.

12. The tri(platinum) complex of claim 11, wherein the substituted malonate has the general formula:

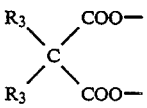

the two $R_3$ groups may be the same or different and are selected from the group consisting of hydrogen (with the proviso that both $R_3$ cannot be hydrogen), $C_1$–$C_8$ linear or branched alkyl groups, or both $(R_3)_2$ groups taken together represent a $C_3$–$C_6$ cycloalkyl group or a CHOH group.

13. The tri(platinum) complex of claim 12, wherein the linear or branched alkyl groups are selected from the group consisting of methyl, ethyl, n-propyl, iso-propyl, n-butyl, sec-butyl, tert-butyl, n-pentyl, n-hexyl, n-heptyl, and n-octyl.

14. The tri(platinum) complex of claim 1, wherein the diamine bridging agent has the general formula $H_2N$—R—$NH_2$ and R is a linear or branched $C_1$–$C_{18}$ alkyl or alkenyl group, cycloalkyl group, substituted phenyl, aralkyl, or perfluoroalkyl group.

15. The tri(platinum) complex of claim 13, wherein the diamine A has the general formula:

NH(R)—$(CH_2)_q$—$R_2$—$(CH_2)_r$—(R)NH wherein R includes the groups set forth in claim 13, q and r are integers ranging from 1 and 4 inclusive, and $R_2$ is selected from the group consisting of —$CH_2$—, —CHOH—, —CO—, —OC(O)(O)—, —$SO_2$—, —OS($O_2$)O—, and —OP(O)(OH)O—.

16. The tri(platinum) complex of claim 13, wherein the diamine bridging agent has the general formula —$NH_2$—$(CH_2)_s$—$NH_2$ and s is an integer ranging from 2 to 9 inclusive.

17. The tri(platinum) complex of claim 1, wherein the counterions P are selected from the group consisting of $Br^-$, $Cl^-$, $I^-$, $NO_3^-$, $SO_4^{2-}$, $ClO_4^-$, carboxylates, $PF_6^-$, and $SbF_6^-$.

18. The tri(platinum) complex of claim 1 which has the general formula (III) and wherein A has a triamine bridging agent having the general formula:

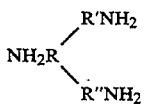

wherein R, R' and R" may be the same or different and are selected from the group consisting of linear or branched alkyl or alkenyl groups, cycloalkyl groups, substituted phenyl groups, aralkyl groups and perfluoroalkyl groups.

19. The tri(platinum) complex of claim 18, wherein A is:

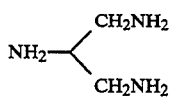

20. A tri(platinum) Pt(IV) complex having the general formula:

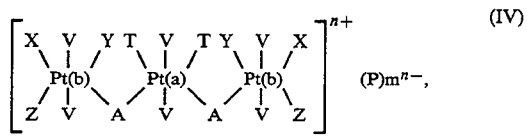

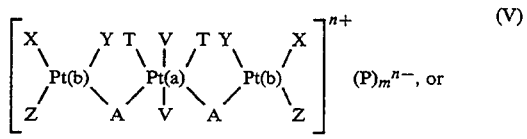

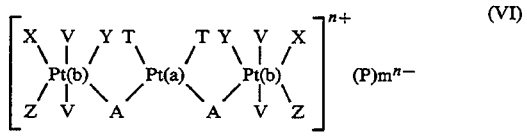

wherein X, Y, Z and T are neutral and/or anionic ligands which may be the same or different, with the proviso that at least one of X, Y or Z on each Pt(b) must be an anionic ligand comprises an anionic group, A is a diamine bridging agent, n represents the net charge of the three platinum coordination spheres, P represents one or more counterions which may or may not be present depending upon whether the three platinum coordination spheres have a net charge, and $n-$ represents the net charge of the counterions and is selected such that the resultant tri(platinum) complex is neutral.

21. The tri(platinum) complex of claim 20, wherein the neutral ligands are selected from the group consisting of $NH_3$, primary amines, secondary amines, heterocyclic amines and sulfoxides.

22. The tri(platinum) complex of claim 21, wherein the heterocyclic amines are selected from the group consisting of pyridine, quinoline, isoquinoline, imidazole, thiazole, piperazine, pyrrolidine, morpholine and N-alkyl or N-acyl-piperazine.

23. The tri(platinum) complex of claim 21, wherein the primary amine has the general formula $NH_2-R_1$ and $R_1$ is selected from the group consisting of linear or branched $C_1-C_8$ alkyl groups, $C_3-C_6$ cycloalkyl groups and —CHOH.

24. The tri(platinum) complex of claim 23, wherein the cycloalkyl groups are selected from the group consisting of cyclopropyl, cyclobutyl, cyclopentyl and cyclohexyl.

25. The tri(platinum) complex of claim 21, wherein the secondary amine has the general formula $NH(R_1)_2$ and $R_1$ is selected from the group consisting of $C_1-C_8$ linear or branched alkyl groups, $C_3-C_6$ cycloalkyl groups and a —CHOH group.

26. The tri(platinum) complex of claim 21, wherein the sulfoxides have the general formula R'R"SO and R' and R" may be the same or different and are selected from the group consisting of methyl, phenyl, substituted phenyl, methylphenyl, ethyl, n-propyl, isopropyl and n-butyl.

27. The tri(platinum) complex of claim 20, wherein the anionic ligands are selected from the group consisting of halides, pseudohalides, carboxylates, mono- and divalent anions.

28. The tri(platinum) complex of claim 20, wherein V is an anionic group selected from the group consisting of $OH^-$, $Cl^-$, and $O_2CR$—wherein R is a linear or branched alkyl group, a cycloalkyl group, an aromatic group or an aralkyl group.

29. The tri(platinum) complex of claim 27, wherein the carboxylate groups are selected from the group consisting of acetate, propionate, butyrate, chloroacetate, hydroxyacetate, benzoate, and chelating dicarboxylate groups.

30. The tri(platinum) complex of claim 29, wherein the chelating dicarboxylate groups are selected from the group consisting of oxalate, malonate, substituted malonate, succinate, glutarate and phthalate.

31. The tri(platinum) complex of claim 30, wherein the substituted malonate has the general formula:

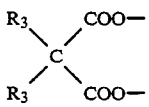

and the two $R_3$ groups may be the same or different and are selected from the group consisting of hydrogen (with the proviso that both $R_3$ cannot be hydrogen), $C_1-C_8$ linear or branched alkyl groups or both $(R_3)_2$ groups taken together represent a $C_3-C_6$ cycloalkyl group or a —CHOH group.

32. The tri(platinum) complex of claim 20, wherein the diamine bridging agent has the general formula $H_2N-R-NH_2$ and R is a linear or branched $C_1-C_{18}$ alkyl or alkenyl group, a cycloalkyl group, substituted phenyl, aralkyl or a perfluoroalkyl group.

33. The tri(platinum) complex of claim 32, wherein the diamine A has the general formula:

$$NH(R)-(CH_2)_q-R_2-(CH_2)_r-(R)NH$$

and R includes the groups set forth in claim 32, q and r are integers ranging from 1 to 4 inclusive, and $R_2$ is selected from the group consisting of $-CH_2-$, $-CHOH-$, $-CO-$, $-OC(O)(O)$, $-SO_2-$, $-OS(O_2)O-$, and $-OP(O)(OH)O-$.

34. The tri(platinum) complex of claim 20, wherein the diamine bridging agent has the general formula:

$$NH_2-(CH_2)_s-NH_2$$

and s is an integer ranging from 2 to 9 inclusive.

35. A method for making the tri(platinum) complex of claim 1 comprising:
  (1) preparing a precursor platinum Pt(a) monomer containing two mono-protected diamine bridging agents wherein one end of each diamine-bridging agent is uncomplexed and comprises either a blocking agent or a $NH_3+$ salt;
  (2) treating said precursor platinum Pt(a) monomer to produce the corresponding protonated amine; and
  (3) reacting said protonated precursor platinum monomer with two equivalents of an appropriate Pt(b) target molecule.

36. The method of claim 35, wherein the precursor platinum monomer is selected from the group consisting of: cis or trans-$[PtCl_2(H_2N-R-NH_3Cl)_2]$, cis or trans-$[Pt(NH_3)_2(H_2N-R-NH_3Cl)_2]^{2+}$, cis or trans-$[PtCl_2(H_2N-R-NH_3Cl)_2]^{2+}$, cis or trans-$[PtCl_2(H_2N-CH(CH_2NH_2)_2Cl_2]$, cis or trans-$[PtCl(NH_3)(H_2N-R-NH_3Cl)_2]+$, and cis-$[Pt(mal)(H_2N-R-NH_3Cl)_2]$ (wherein mal is malonate or a dicarboxylate), and wherein R is a linear or branched alkyl or alkenyl group, a cycloalkyl group, a substituted phenyl group, an aralkyl group, or a perfluoroalkyl group.

37. The method of claim 35, wherein the Pt(b) target molecule has the general formula: $[PtLCl_3]-$, wherein L is $NH_3$, a primary amine, sulfoxide or pyridine.

38. The method of claim 35, wherein the Pt(b) target molecule is selected from the group consisting of cis- or trans-$[PtCl_2(NH_3)_2]$, and cis- or trans-$[PtCl_2(RNH_2)_2]$, wherein R is a linear or branched alkyl or alkenyl group, a cycloalkyl group, a substituted phenyl group, an aralkyl group, or a perfluoroalkyl group.

39. The tri(platinum) complex of claim 1 which has cis-$[\{cis-PtCl_2(NH_3)(\mu-H_2N(CH_2)_4NH_2)\}_2PtCl_2]$.

40. The tri(platinum) complex of claim 1 which has cis-$[\{cis-Pt(mal)(NH_3)(\mu-H_2N(CH_2)_4NH_2)\}_2Pt(mal)]$ wherein mal is malonate.

41. The tri(platinum) complex of claim 1 which has cis-$[\{cis-PtCl_2(NH_3)(\mu-H_2N(CH_2)_4NH_2)\}_2Pt(NH_3)_2]Cl_2$.

42. The tri(platinum) complex of claim 1 wherein the tri(platinum) complex has the general formula (I) wherein two of X, Y and Z are anionic ligands.

43. The tri(platinum) complex of claim 42 wherein said anionic ligands are chloride ions.

44. The tri(platinum) complex of claim 43 wherein T is $NH_3$.

45. The tri(platinum) complex of claim 44 wherein P is chloride.

46. The tri(platinum) complex of claim 42 wherein n is 2 or zero.

47. The tri(platinum) complex of claim 43 wherein n is 2 or zero.

48. The tri(platinum) complex of claim 45 wherein n is 2 or zero.

* * * * *